(12) United States Patent
O'Hara et al.

(10) Patent No.: US 6,669,621 B2
(45) Date of Patent: Dec. 30, 2003

(54) METHOD AND ASSEMBLY FOR CONTAINING RADIOACTIVE MATERIALS

(75) Inventors: Michael Dennis O'Hara, Stewartsville, NJ (US); Benjamin David McDaniel, Newport Beach, CA (US)

(73) Assignee: Cordis Corporation, Miami Lakes, FL (US)

( * ) Notice: Subject to any disclaimer, the term of this patent is extended or adjusted under 35 U.S.C. 154(b) by 313 days.

(21) Appl. No.: 09/805,961

(22) Filed: Mar. 14, 2001

(65) Prior Publication Data

US 2003/0220534 A1 Nov. 27, 2003

(51) Int. Cl.[7] .............................. A61M 36/00
(52) U.S. Cl. .................. 600/7; 600/1; 600/3; 600/8
(58) Field of Search ................. 600/1, 3, 7, 8

(56) References Cited

U.S. PATENT DOCUMENTS

| | | | |
|---|---|---|---|
| 1,718,899 A | * 6/1929 | Fischer | 427/5 |
| 3,351,049 A | * 11/1967 | Lawrence | 600/8 |
| 4,323,055 A | 4/1982 | Kubiatowicz | |
| 4,737,153 A | 4/1988 | Shimamura et al. | |
| 4,994,013 A | 2/1991 | Suthanthiran et al. | |
| 5,059,166 A | 10/1991 | Fischell et al. | |
| 5,163,896 A | 11/1992 | Suthanthiran et al. | |
| 5,199,939 A | 4/1993 | Dake et al. | |
| 5,454,795 A | 10/1995 | Samson | |
| 5,863,284 A | 1/1999 | Klein | |
| 5,871,436 A | 2/1999 | Eury | |
| 5,873,811 A | 2/1999 | Wang et al. | |
| 5,882,291 A | 3/1999 | Bradshaw et al. | |
| 5,899,882 A | 5/1999 | Waksman et al. | |
| 5,976,067 A | 11/1999 | Tucker et al. | |
| 6,007,475 A | 12/1999 | Slater et al. | |
| 6,019,718 A | 2/2000 | Hektner | |
| 6,036,682 A | 3/2000 | Lange et al. | |
| 6,059,714 A | 5/2000 | Armini et al. | |
| 6,077,213 A | 6/2000 | Ciezki et al. | |
| 6,096,070 A | 8/2000 | Ragheb et al. | |
| 6,103,295 A | 8/2000 | Chan et al. | |
| 6,132,359 A | 10/2000 | Bolenbaugh | |
| 6,149,574 A | 11/2000 | Trauthen et al. | |
| 6,156,046 A | 12/2000 | Passafaro et al. | |
| 6,159,143 A | 12/2000 | Lennox | |

* cited by examiner

Primary Examiner—Thomas Denion
Assistant Examiner—Theresa Trieu
(74) Attorney, Agent, or Firm—Carl Evens

(57) ABSTRACT

A radioactive substance absorber is incorporated into an intravascular radiotherapy source ribbon assembly to prevent the migration of radioactive matter throughout the assembly container. The radioactive substance absorber comprises carbon in various forms and configurations. The radioactive substance absorber is positioned in proximity to the source core and absorbs radioactive materials which break free from the source core, thereby containing the radioactive material.

12 Claims, 5 Drawing Sheets

METHOD AND ASSEMBLY FOR CONTAINING RADIOACTIVE MATERIALS

BACKGROUND OF THE INVENTION

1. Field of the Invention

The present invention relates to brachytherapy devices, and more particularly to a method and assembly for containing the radioisotopes or other radioactive materials utilized in brachytherapy devices.

2. Discussion of the Related Art

Percutaneous transluminal coronary angioplasty (PTCA) is a therapeutic medical procedure used to increase blood flow through an artery and is the predominant treatment for coronary vessel stenosis. The increasing popularity of the PTCA procedure is attributable to its relatively high success rate and its minimal invasiveness compared with coronary by-pass surgery. Patients treated utilizing PTCA; however, may suffer from restenosis. Restenosis refers to the re-narrowing of an artery after a successful angioplasty procedure. Restenosis usually occurs within the initial six months after an angioplasty. Early attempts to alleviate the effect of restenosis included repeat PTCA procedures or by-pass surgery, with attendant high cost and added patient risk.

More recent attempts to prevent restenosis by use of drugs, mechanical devices, and other experimental procedures have limited long term success. Stents, for example, dramatically reduce acute reclosure and slow the effects of smooth muscle cell proliferation by enlarging the maximal luminal diameter, but otherwise do nothing substantial to slow the proliferative response to the angioplasty induced injury.

Restenosis is now believed to occur at least in part as a result of injury to the arterial wall during the lumen opening angioplasty procedure. In some patients, the injury initiates a repair response that is characterized by hyperplastic growth of the vascular smooth muscle cells in the region traumatized by the angioplasty. Intimal hyperplasia or smooth muscle cell proliferation narrows the lumen that was opened by the angioplasty, regardless of the presence of a stent, thereby necessitating a repeat PTCA or use of other procedures to alleviate the restenosis.

Recent studies indicate that intravascular radiotherapy (IRT) has promise in the prevention or long-term control of restenosis following angioplasty. Intravascular radiotherapy may also be used to prevent or delay stenosis following cardiovascular graft procedures or other trauma to the vessel wall. Proper control of the radiation dosage, however, appears to be important to inhibit or substantially arrest hyperplasia without causing excessive damage to healthy tissue. Underdosing will result in inadequate inhibition of smooth muscle cell hyperplasia, or possibly even exacerbation of hyperplasia and resulting restenosis.

Radiation therapy may also be utilized in the treatment of other diseases such as cancerous and non-cancerous tumors or other proliferative normal tissue disorders. In this type of therapy, the ultimate aim is to destroy the malignant tissue without causing excessive radiation damage to nearby healthy, and possibly vital tissue. This is difficult to accomplish because of the proximity of malignant tissue to healthy tissue.

Brachytherapy is a form of radiation treatment in which an ionizing radiation source, for example, an intravascular radiotherapy source ribbon, is placed into or adjacent to a tumor or stenotic lesion. Although any number of radioactive substances and/or radioactive sources may be utilized in brachytherapy, Iodine-125 is currently a good candidate isotope for vascular brachytherapy. Iodine-125 has been used as a liquid or immobilized onto a variety of surfaces for diagnostic and therapeutic purposes. It has already been fashioned into a variety of shapes and used clinically for cancer treatment as briefly described above. One standard method for immobilizing Iodine-125 on to a solid surface is through electroplating. Currently, Iodine-125 is immobilized onto the surface of solid silver wires for a very secure bond. Silver is specifically utilized because of the extremely secure bond it forms with the Iodine-125; however, impurities and the like may cause the Iodine-125 to "break free" from the silver regardless of how strong the bond and potentially create a contamination problem.

SUMMARY OF THE INVENTION

The method and assembly for containing radioactive materials of the present invention provides a means for overcoming the difficulties associated with the devices currently in use as briefly described above.

In accordance with one aspect, the present invention is directed to a method for containment of radioactive substances in an intravascular radiotherapy source ribbon assembly. The method comprises positioning a radioactive substance absorber in proximity to a radioactive source core; and sealing the radioactive substance absorber and radioactive source core in a radiation transparent container.

In accordance with another aspect, the present invention is directed to an intravascular radiotherapy source ribbon assembly. The assembly comprises a sealed, elongated flexible tube defining an interior cavity, a radioactive source core disposed within the interior cavity, and a radioactive substance absorber disposed in proximity to the source core to absorb stray radioactive matter.

The method and assembly for containing radioactive materials of the present invention comprises utilizing carbon in any number of forms and any number of configurations as a means for absorbing free radioactive materials. A typical intravascular radiotherapy source ribbon comprises a source core disposed within a radio-transmissive, sealed container. It is possible that particles, salts or gaseous forms of the radioactive substance comprising the core may break free from the core and migrate through the outer components of the ribbon. The incorporation of carbon fiber, or the like, in the wall of the container, or as a layer adjacent to the source, would serve as a radioactive substance absorber as well as strengthen the polymer. As the radioactive material contamination permeates the assembly, the carbon would serve as an absorption point and slow the transmission of contaminants to the surface by bonding them to the carbon through absorption. Since the radioactive substance is slowed prior to reaching the surface, the chance of spreading the contaminants is substantially reduced. This technique could be thought of as a "belt and suspenders" approach to improve the radiation safety of any radioactive liquid or gas based radiotherapy device.

BRIEF DESCRIPTION OF THE DRAWINGS

The foregoing and other features and advantages of the invention will be apparent from the following, more particular description of preferred embodiments of the invention, as illustrated in the accompanying drawings.

DETAILED DESCRIPTION OF THE PREFERRED EMBODIMENTS

Figure 1:
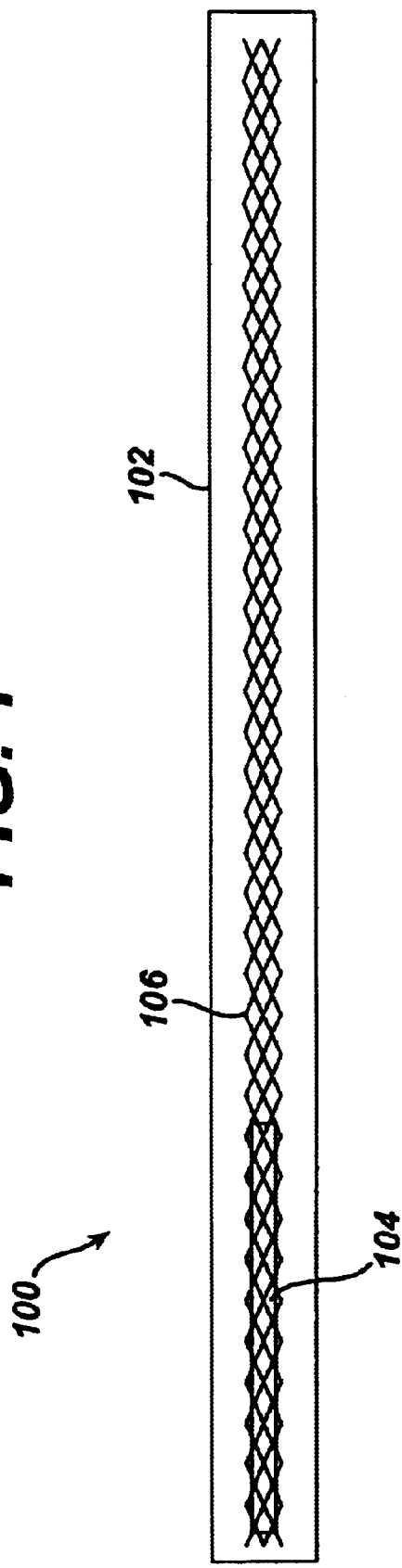
FIG. 1 is a cross-sectional view of a first exemplary, embodiment of an intravascular radiotherapy source ribbon assembly in accordance with the present invention.

The method and assembly for containing radioisotopes of the present invention comprises utilizing various forms of carbon as a secondary or backup radiation source containment means. In the exemplary embodiments described in detail below, carbon or carbon fibers are integrated into an intravascular radiotherapy source ribbon assembly in order to ensure containment of any radioactive materials which separate from the core and in the unlikely event that the assembly container develops a breach. The carbon, as set forth in detail subsequently, may be utilized in a variety of forms, for example, powder, pellets, or fiber, and in a variety of configurations to not only act as a containment means, but also to potentially provide additional structural support for the assembly.

A typical intravascular radiotherapy source ribbon assembly comprises a radioactive source disposed in a cavity of a substantially tubular container. The radioactive source may include any therapeutic amount of radioactive material appropriately distributed on a carrier body or core. The container is sealed at its ends and functions to isolate the radioactive substance from physical or chemical interchange between bodily fluids and the interior of the container, while at the same time permitting the radiation to pass through the walls of the container with minimum attenuation. The container, which may be formed from any number of suitable materials, including Nylon®, may be delivered to the site of the stenotic lesion or malignant cells by any number of suitable delivery devices, e.g. catheters, which are known in the art.

The carrier body or core may be formed from any suitable material which is detectable by x-rays for proper positioning in the body, and to which the requisite therapeutic amount of radioactive material may be attached. In the exemplary embodiments described below, the carrier body or core comprises at least one section or length of solid silver wire, or silver plated wire, and the radioactive material comprises radioisotopes such as Iodine-125 and Iodine-131. It is important to note that other radioactive substances may be utilized. Iodine-125, as stated above, is preferred because of its energetic emission of photons and its ability to strongly bond with silver.

Silver is the material of choice for a carrier body or core because it provides good x-ray visualization, which is important for proper positioning of the seed during therapy and because radioactive iodine may be easily attached to the surface thereof by chemical or electroplating processes. It is obvious that other x-ray opaque materials such as gold, copper and iron may be plated with silver to form a carrier body equivalent to a solid silver rod for purposes of the present invention. Similarly, silver metal may be deposited, chemically or by using sputtering and ion plating techniques, onto a substrate other than metal, for example, polymers such as polypropylene filament, provided that the thickness of the silver coating on the substrate exceeds about 0.050 mm to ensure adequate x-ray visualization.

Radioactive iodine may be attached to a silver substrate by a variety of suitable means, such as by first chloriding or bromiding the silver to form a layer of insoluble silver chloride or silver bromide, and then replacing the chloride or bromide ions with radioactive iodine ions by simple ion exchange. This process as well as other processes are well known in the relevant art.

Although radioactive iodine forms a very strong bond with silver, it is potentially possible for the radioactive iodine to break free from the silver through various mechanisms such as sublimation. For example, if during the above-described bonding process impurities become involved, the iodine/silver bond may not be as strong as if no impurities were involved. Accordingly, an intravascular radiotherapy source ribbon that comprises radioactive iodine has the potential for allowing particles, salts or gaseous forms of radioactive iodine to break free from the core and migrate through the container. Although the container is sealed, as described above, the present invention provides a secondary means of containment in the unlikely event of a breach in the container. The secondary means of containment comprises the use of carbon fibers to absorb any radioactive material that breaks free from the core. Carbon is utilized because it is extremely radiation resistant in that it will not break down under constant bombardment from radioactive emissions, it lasts for a relatively long time, and it readily absorbs and binds the free radioactive iodine. In addition, carbon absorbs only a minimal amount of emitted photons, typically much less than the silver core, thus minimally adding to the attenuation factor of the core. Other materials may be utilized as an iodine absorber; however, for the reasons discussed above, carbon is preferred.

Essentially, the incorporation of carbon in the walls of the container or as a layer adjacent to the source core, would serve as a radioactive iodine absorber. As the iodine contamination permeates the device, the carbon would serve as an absorption point and slow the transmission of iodine contaminants to the surface by bonding them to the carbon fiber at a layer below the outer surface of the assembly. Since the radioactive iodine is slowed prior to reaching the surface of the container, the chance of spreading the contamination is substantially reduced.

Referring to FIG. 1, there is illustrated a first exemplary embodiment of an intravascular radiotherapy source ribbon assembly 100 incorporating a carbon containment means in accordance with the present invention. The intravascular radiotherapy source ribbon assembly 100 comprises a substantially tubular container 102, a radioactive source core 104 disposed within the cavity defined by the container 102, and a carbon fiber layer 106 substantially encasing the radioactive source core 104. The container 102 is sealed at both its proximal and distal ends to isolate the radioactive source core 104 and may be formed from any suitable biocompatible and radioactive emission transparent material. In addition, the container 102 is preferably flexible enough to navigate through narrow and/or tortuous pathways and stiff enough to traverse the same narrow and/or tortuous pathways. In the preferred embodiment, the container 102 is formed from Nylon®. The radioactive source core 104, as described above, comprises one or more sections or lengths of silver wire or silver coated metallic or non-metallic substrate, and a radioactive substance distributed on the one or more sections or lengths of silver wire.

The cross-section of the silver wire may be varied to increase the surface area available on which to dispose the radioactive substance. Although any number of radioactive materials producing ionizing radiation may be utilized, in the preferred embodiment Iodine-125 is utilized because of its energetic emission of photons and its ability to strongly bond with silver. The carbon fiber layer 106 substantially encasing the radioactive source core 104 may comprise a number of configurations. In the exemplary embodiment illustrated in FIG. 1, the carbon fiber layer 106 comprises strands of carbon fibers interwoven into a sheath into which the radioactive source core 104 may be disposed. Any suitable mesh-like patterns may be utilized. The mesh design of the carbon fiber layer 106 provides the requisite coverage for absorption of stray radioactive components while minimally attenuating the emissions thereof. As stated above, the ability to absorb stray radioactive components is important to reduce the amount of radioactive contaminates free in the cavity of the container 102 of the radioactive iodine based intravascular radiotherapy source ribbon assembly 100. In this exemplary embodiment, the carbon fiber layer 106 is essentially a discrete component of the assembly 100; however, as described below other configurations may be possible.

Figure 2:
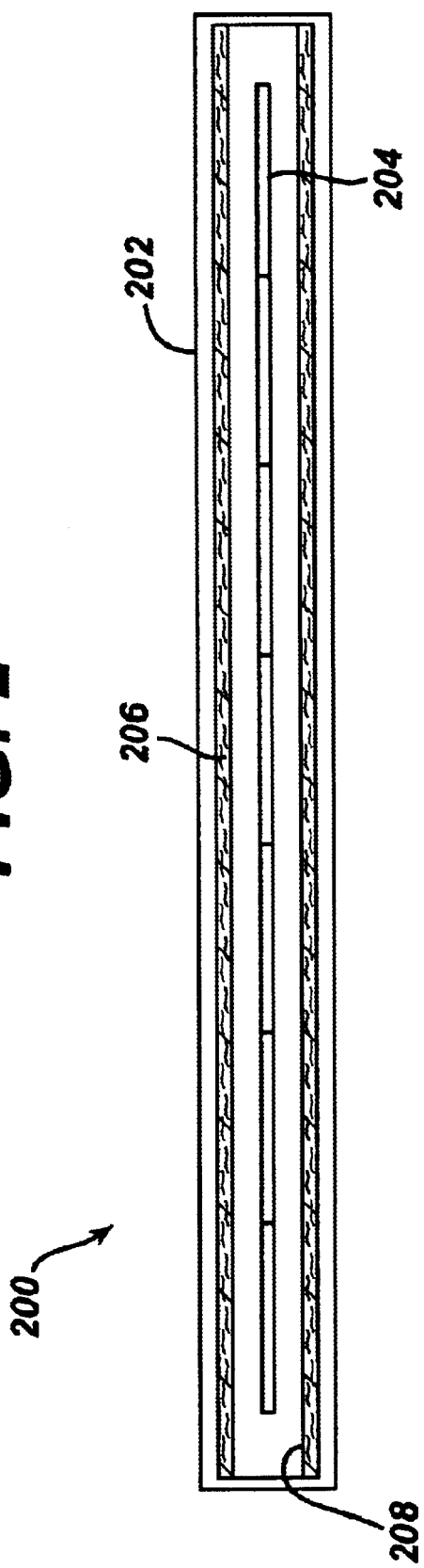
FIG. 2 is a cross-sectional view of a second exemplary embodiment of an intravascular radiotherapy source ribbon assembly in accordance with the present invention.

In an alternate exemplary embodiment, the carbon fiber layer may be integrated into or attached to the wall of the container. For example, as illustrated in FIG. 2, the intravascular radiotherapy source ribbon assembly 200 comprises a substantially tubular container 202, a radioactive source core 204 disposed within the cavity defined by the container 202, and a carbon fiber layer 206 integrated into the wall 208 of the container 202. The carbon fiber layer 206 may be integrated into the wall 208 in any number of ways, including, simply sandwiching it between two layers of the material forming the container 202. Alternately, the carbon fiber layer 206 may be integrated into the wall 208 of the container 202 by attaching it to the inner surface of the wall 208. The carbon fiber layer 206 may be attached to the wall 208 by any suitable means, including chemical and mechanical bonding. In either of these configurations, the carbon fiber layer 206 not only provides a means for containment of stray radioactive materials, but also adds a new dimension of structural support. Essentially, the carbon fiber layer 206 adds strength to the container 202.

Figure 3:
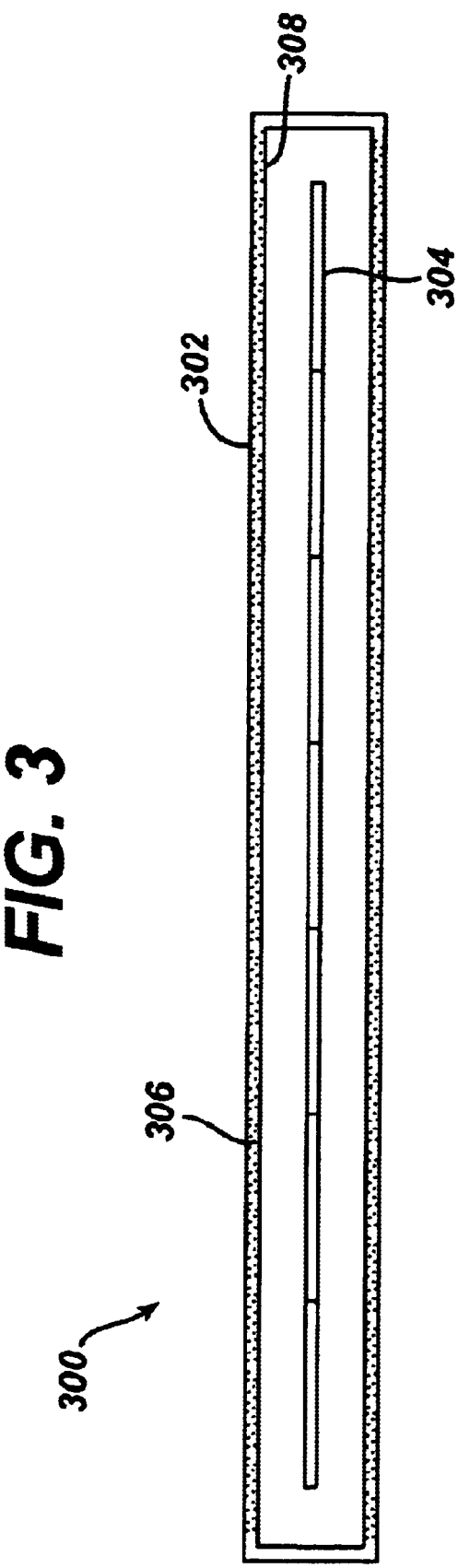
FIG. 3 is a cross-sectional view of a third exemplary embodiment of an intravascular radiotherapy source ribbon assembly in accordance with the present invention.

In another alternate exemplary embodiment, carbon powder may be utilized rather than interwoven carbon fibers. For example, carbon powder may be suspended from any of the components comprising the source ribbon assembly. FIG. 3 illustrates an intravascular radiotherapy source ribbon assembly 300, which comprises carbon powder particles 306 suspended from the wall 308 of the container 302. The carbon powder particles 306 may be suspended from the wall 308 of the container 302 by any suitable means. For example, the carbon powder particles 306 may be impregnated into the wall 308. The carbon powder particles 306 would absorb stray radioactive materials which break free from the radioactive source core 304 in a manner analogous to the carbon fiber layers discussed above.

In a typical intravascular radiotherapy source ribbon assembly, the radioactive source core may comprise a number of sections of radioactive material covered wires. These individual sections are typically referred to as seeds. The seeds may be adjacent one another in the container or they may be spaced apart by any suitable means. Accordingly, the carbon fiber layers discussed above with respect to FIGS. 1 and 2 may cover the entire length of the source core, or cover only the "hot" sections of the core. Likewise, the carbon powder particles may be evenly distributed along the length of the source core, or may be concentrated over the "hot" sections.

Figure 4:
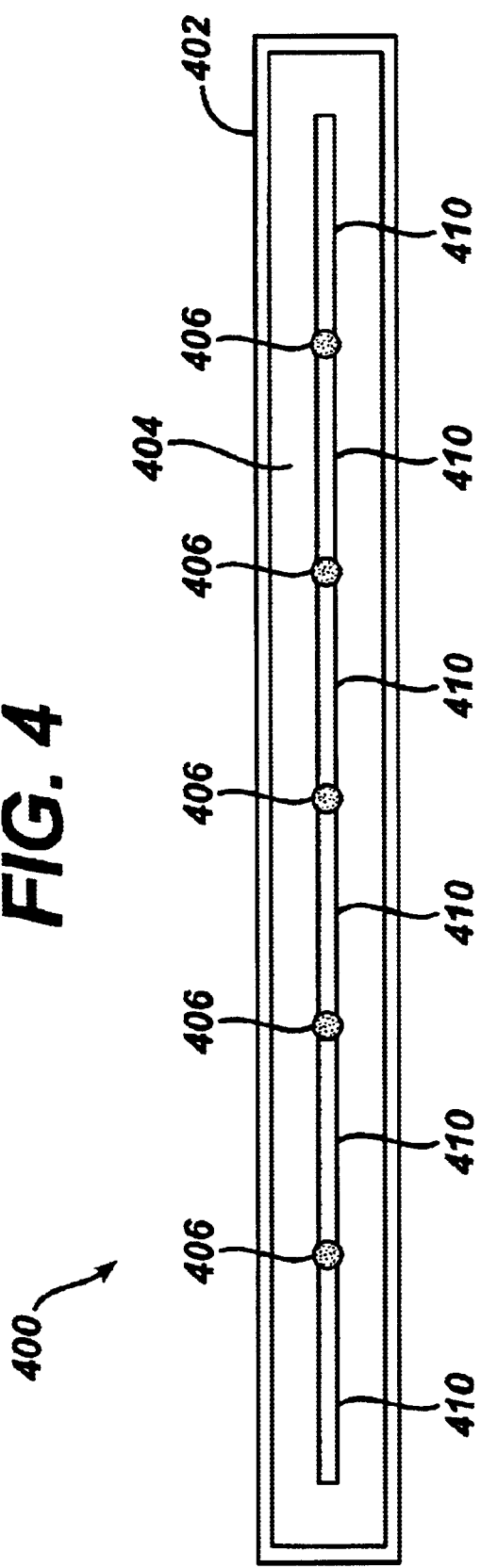
FIG. 4 is a cross-sectional view of a fourth exemplary embodiment of an intravascular radiotherapy source ribbon assembly in accordance with the present invention.

As described above, the seeds forming the source core may be positioned adjacent one another or spaced apart by any suitable means. The spacers serve two main functions. The first function is to space the "hot" seeds a sufficient distance to control the dose rate profile and lower the total radioactivity of the source core. The second function is to increase the flexibility of the source ribbon assembly. Accordingly, in another alternate exemplary embodiment, carbon may be formed into pellets or the like and used as the spacers between "hot" seeds. In utilizing a pellet or ball bearing type shape, the flexibility of the source ribbon assembly may be increased. FIG. 4 illustrates an intravascular radiotherapy source ribbon assembly 400 comprising carbon pellets 406 positioned between radioactive seeds 410 forming the radioactive source core 404. The carbon pellets 406 may be positioned between each seed 410 or between only certain seeds 410 to achieve the optimum profile as described above. The carbon pellets 406 preferably absorb stray radioactive materials in a manner analogous to the exemplary embodiments described above.

Figure 5:
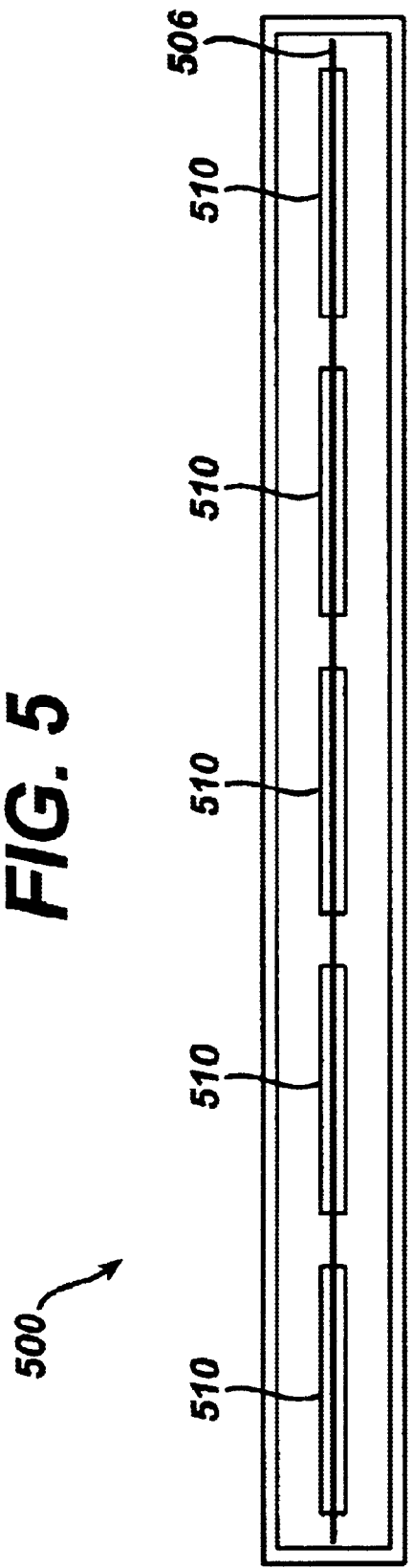
FIG. 5 is a cross-sectional view of a fifth exemplary embodiment of an intravascular radiotherapy source ribbon assembly in accordance with the present invention.

In another alternate exemplary embodiment, the seeds may comprise holes therethrough and strung on a thread or other elongate member formed from carbon. Referring to FIG. 5, there is illustrated an intravascular radiotherapy source ribbon assembly 500 comprising a plurality of radioactive seeds 510 having a carbon thread 506 extending therethrough. As illustrated, the thread 506 serves as the core upon which the source material may be suspended to form an assembly 500 similar to a "string of pearls" where the "string" would serve the purpose of stray source absorption.

Although shown and described is what is believed to be the most practical and preferred embodiments, it is apparent that departures from specific designs and methods described and shown will suggest themselves to those skilled in the art and may be used without departing from the spirit and scope of the invention. The present invention is not restricted to the particular constructions described and illustrated, but should be constructed to cohere with all modifications that may fall within the scope of the appended claims.

What is claimed is:

1. A method for the containment of radioactive substances in an intravascular radiotherapy source ribbon assembly comprising:

positioning a radioactive substance absorber in proximity to a radioactive source core, including disposing a carbon fiber layer sheath over the radioactive source core; and sealing the radioactive substance absorber and radioactive source core in a flexible, radiation transparent container of the intravascular radiotherapy source ribbon assembly.

2. The method for containment of radioactive substances in an intravascular radiotherapy source ribbon assembly according to claim 1, wherein the step of positioning comprises integrating a carbon fiber layer sheath into a wall of the container.

3. The method for containment of radioactive substances in an intravascular radiotherapy source ribbon assembly according to claim 1, wherein the step of positioning comprises suspending carbon powder in a wall of the container.

4. The method for containment of radioactive substances in an intravascular radiotherapy source ribbon assembly according to claim 1, wherein the step of
positioning comprises positioning carbon pellets between elements comprising the source core.

5. The method for containment of radioactive substances in an intravascular radiotherapy source ribbon assembly according to claim 1, wherein the step of positioning comprises disposing a carbon fiber strand through the source core.

6. An intravascular radiotherapy source ribbon assembly comprising:
- a sealed, elongated flexible tube defining an interior cavity;
- a radioactive source core disposed within the interior cavity; and
- a radioactive substance absorber disposed in proximity to the source core to absorb stray radioactive matter, around the radioactive source core the radioactive substance absorber comprises a carbon fiber layer disposed around the radioactive source core.

7. The intravascular radiotherapy source ribbon assembly according to claim 6, wherein the radioactive source core comprises one or more radioactive seeds.

8. The intravascular radiotherapy source ribbon assembly according to claim 7, wherein the one or more radioactive seeds comprise radioactive isotopes.

9. The intravascular radiotherapy source ribbon assembly according to claim 8, wherein the radioactive substance absorber comprises carbon pellets disposed between the one or more radioactive seeds.

10. The intravascular radiotherapy source ribbon assembly according to claim 6, wherein the radioactive substance absorber comprises a carbon fiber layer sheath integrated into a wall of the sealed, elongated flexible tube.

11. The intravascular radiotherapy source ribbon assembly according to claim 6, wherein the radioactive substance absorber comprises carbon powder suspended in a wall of the sealed, elongated flexible tube.

12. The intravascular radiotherapy source ribbon assembly according to claim 8, wherein the radioactive substance absorber comprises a carbon fiber strand disposed within the one or more radioactive seeds.

* * * * *